US00PP11627P

United States Patent [19]

Vijverberg

[11] Patent Number: Plant 11,627

[45] Date of Patent: Nov. 7, 2000

[54] CHRYSANTHEMUM PLANT NAMED 'VYMINI'

[75] Inventor: Arnold Vijverberg, 's-Gravenzande, Netherlands

[73] Assignee: Vyking Flowers B.V., Netherlands

[21] Appl. No.: 09/150,677

[22] Filed: Sep. 10, 1998

[51] Int. Cl.[7] ..... A01H 5/00

[52] U.S. Cl. ..... Plt./295

[58] Field of Search ..... Plt./286, 295

*Primary Examiner*—Howard J. Locker

[57] ABSTRACT

A new and distinct cultivar of chrysanthemum plant named Vymini, bearing small sized blooms with yellow ray florets and a brown center and performance of 14 days.

2 Drawing Sheets

BACKGROUND OF THE INVENTION

The present invention comprises a new and distinct cultivar of chrysanthemum plant that is a natural occuring sport of a parent chrysanthemum named Regoltime. Parent chrysanthemum Regoltime is also described in this application. The new cultivar was discovered as a whole plant mutation in 1992 by Arnold Vijverberg in a controlled environment (greenhouse) in 's-Gravenzande, Holland. The first act of asexual reproduction of Vymini was accomplished when vegetative cuttings were taken from the initial selection in May 1992 in 's-Gravenzande, Holland.

SUMMARY OF THE INVENTION

The present invention is a new and distinct variety bearing small sized blooms with yellow ray florets and a brown center.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
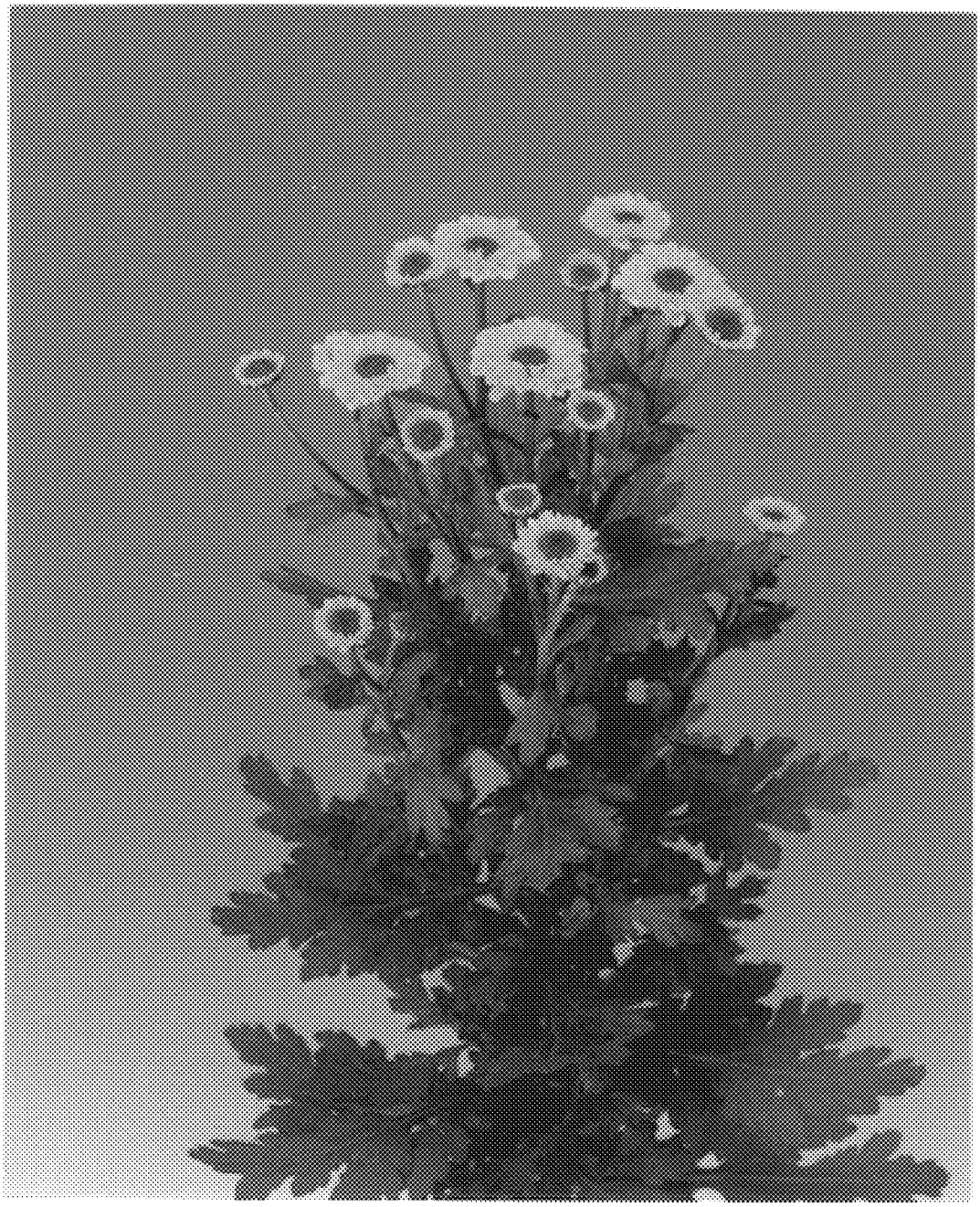
FIG. 1 shows the stem of the cultivar in full bloom.
Figure 2:
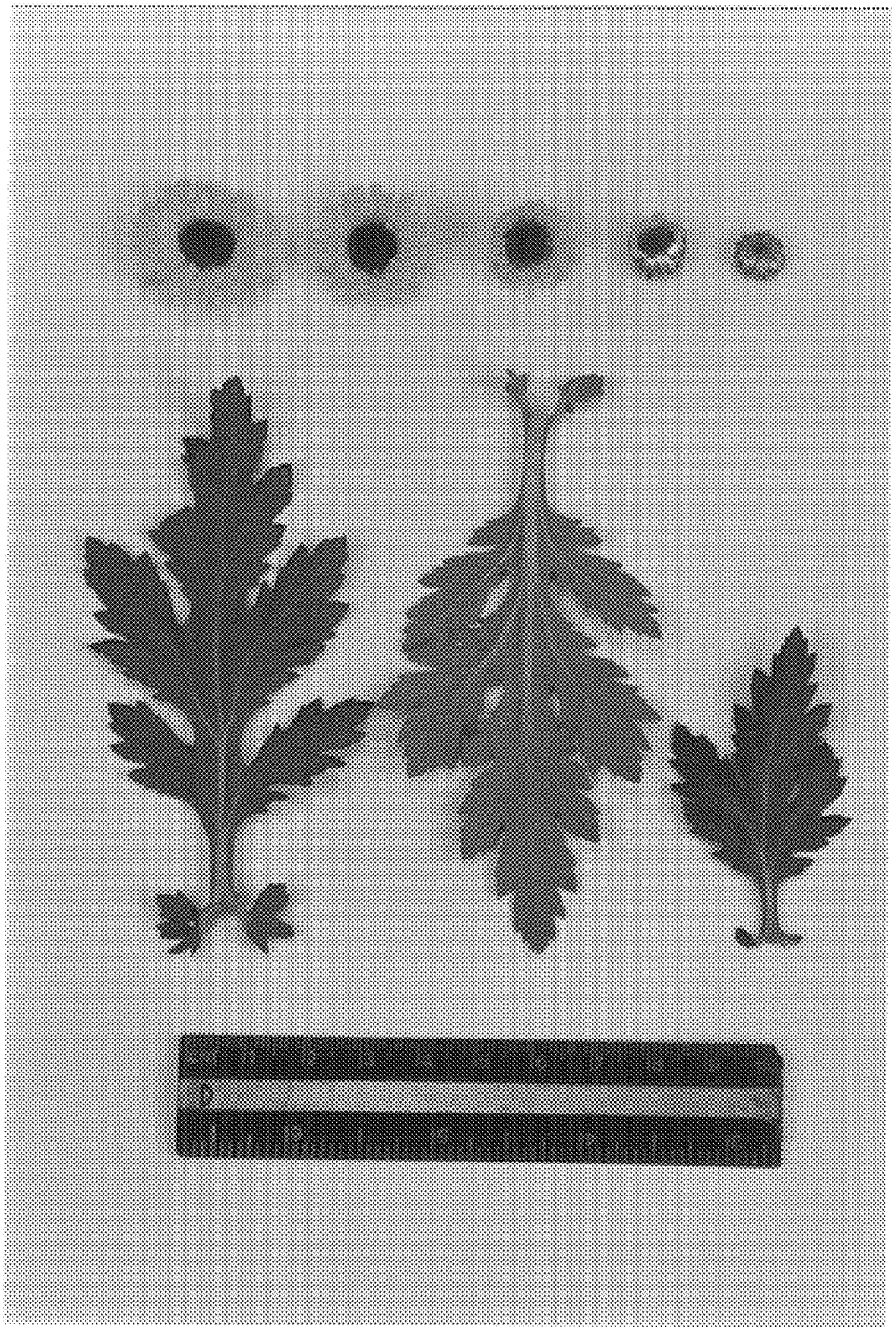
FIG. 2 shows the various stages of bloom and foliage of the new cultivar.

This new variety of chrysanthemum is of the botanical classification *Dendranthema grandiflora*. When grown in the vicinity of 's-Gravenzande, Holland, it has a response time of approximately 6.5 weeks. This new variety produces small sized blooms with yellow ray florets and a brown center having a 2 week performance (i.e., vase life of 14 days). This new variety of chrysanthemum has been found to retain its distinctive characteristics throughout successive propagations. However, the phenotype may vary significantly with variations in the environment such as light intensity and temperture. To show the phenotype as described, Vymini may be planted under greenhouse conditions in Holland without assimilation lightning between week 2 and 36. With assimilation lightning (minimum level 2500 lux), Vymini may be planted year round under greenhouse conditions in Holland.

The following is a description of the plant and characteristics (color designations are from R.H.S. Color Chart) that distinguish it from related known varieties and its antecedents:

The color designations are taken from the plant itself. Accordingly, any discrepancies between the color designations and the colors depicted in the photographs are due to photographic tolerances.

Botanical description of Vymini and its parent Regoltime:

| CULTIVAR | VYMINI | Parent Cultivar REGOLTIME |
|---|---|---|
| Bud | | |
| Size | small cross section ±1.0 cm Height ±1.0 cm | large cross section ±1.5 cm height ±1.2 cm |
| Outside Color | yellow 12B | near yellow 7C |
| Bloom | | |
| Size | small | small |
| Fully Expanded | 3–3½ cm | 4½–5 cm |
| Born | upper portion single flower per peduncle, lower portion plural flower per peduncle | upper portion single flower per peduncle, lower portion plural flower per peduncle. |
| Number of blooms per single stem | Average of 22–25 | Average of 10 |
| Peduncle Lengths | near the top ±5 cm near the middle ±8 cm near the bottom ±12 cm | near the top ±6 cm near the middle ±12 cm near the bottom ±16 cm |
| Peduncle Lateral Shoot, Attachment | medium | medium |
| Peduncle Lateral Shoot, Angle | 40°–35° | 35°–30° |
| Form | single (daisy) | single (daisy) |
| Performance (lastingness of the total inflorescence) | reasonable, 14 days (18°–20° C.) | reasonable, 14 days (18°–20° C.) |
| Color | | |
| Center of Flower/ Disc Floret | greyed-orange 173A grading to greyed-purple 187A at the center | Immature: yellow-green 144A Mature: yellow-green 144C |
| Color of the upper surface of the majority of the ray-florets | yellow 13A | Nearest Yellow 9A |
| Color of the lower surface of the majority of the ray-florets | yellow 7B | Between Yellow 6C and Yellow 7C |
| Tonality from Distance | a small yellow daisy with a brown center | A yellow daisy with a green center showing no pollen |

-continued

Botanical description of Vymini and its parent Regoltime:

| CULTIVAR | VYMINI | Parent Cultivar REGOLTIME |
|---|---|---|
| Discoloration | ray-florets almost none, disc-floret after anther dehiscence to yellow tipped with brown | to Yellow 8A |
| Pollen | Not present | Not present |
| Ray florets | | |
| Texture | upper side smooth; under side smooth | upper side smooth, under side smooth. |
| Number | 35–38 (2–3 rows) | 45–50, two rows |
| Cross-section | concave | convex, two keels |
| Longitudinal axis of majority | straight | imbricated |
| Shape of tip | dentate | very good, ray florets keep straight total vase life. |
| Fragrance | typical chrysanthemum | typical chrysanthemum |
| Disc Diameter | small (1.0 cm) | medium (±1.5 cm) |
| Reproductive Organs | | |
| Stamen (present in disc florets only) | yellow-green ±3 mm in length | yellow-green, thick, ±5 mm in length. |
| Pollen | not present | not present |
| Styles (present in disc and ray florets) | green, thin | green, thick |
| Style Length | ±4 mm | ±5 mm |
| Stigmas | yellow-green | yellow-green |
| Stigma Width | ±1 mm | ±2 mm |
| Ovaries | enclosed in calyx | enclosed in calyx |
| Plant | | |
| Form | spray mum meant for erect culture. Herbaceous | spray mum meant for erect culture. Herbaceous. |
| Growth | very short | short |
| Height | ±55 cm | ±100 cm |
| Stem Color | not green: near greyed-purple 187B | yellow-green 146C |
| Stem Strength | very strong | strong |
| Stem Brittleness | present | absent |
| Stem Anthocyanin | present (all over the | absent |

-continued

Botanical description of Vymini and its parent Regoltime:

| CULTIVAR | VYMINI | Parent Cultivar REGOLTIME |
|---|---|---|
| Coloration | stem) | |
| Internodes | very short | very short to short, 1½–2 cm |
| Flowering Response (photoperiodic controlled crop, no natural growing) | 6.5 weeks | 10 weeks |
| Foliage | | |
| Color | upperside yellow-green 144A underside yellow-green 144B | upperside green 137 A, underside green 137 C |
| Size | length ±7 cm; width ±4 cm | length ±12 cm, width ±8 cm |
| Quantity (per single stem) | 35–38 | 28–32 |
| Shape | incurved | incurved |
| Texture | fleshy | upperside fleshy, underside smooth, slightly hirsute |
| Ribs and Veins | ribs and veins well developed | ribs well developed, veins not so developed |
| Edge | crenated | crenated |
| Shape of Base of Sinus Between Lateral Lobes | round | round |
| Margin of Sinus Between Lateral Lobes | converging | converging |
| Shape of Base | truncate | cordate |
| Apex | mucronate | cuspidate |
| Year of Discovery | 1992 | 1980 |

I claim:

1. A new and distinct variety of chrysanthemum plant as described and illustrated.

* * * * *